(12) United States Patent
Youn et al.

(10) Patent No.: US 12,042,317 B2
(45) Date of Patent: Jul. 23, 2024

(54) PORTABLE X-RAY SYSTEM WITH A CABLELESS COLLIMATOR CONNECTION STRUCTURE

(71) Applicant: FSK Co., Ltd., Gimpo-si (KR)

(72) Inventors: Ju Seon Youn, Seoul (KR); Sung Sup Kim, Chuncheon-si (KR); Ha Yeon Youn, Seoul (KR); Ronald Viola, Pittsford, NY (US); Michelle Anne Brown, Fairport, NY (US); David Venniro, Webster, NY (US); Young Il Yoo, Anyang-si (KR); Sang Im Shim, Siheung-si (KR)

(73) Assignee: FSK Co., Ltd., Gimpo-si (KR)

( * ) Notice: Subject to any disclaimer, the term of this patent is extended or adjusted under 35 U.S.C. 154(b) by 0 days.

(21) Appl. No.: 18/401,956

(22) Filed: Jan. 2, 2024

(65) Prior Publication Data
US 2024/0197271 A1   Jun. 20, 2024

(30) Foreign Application Priority Data
Dec. 15, 2022   (KR) .......................... 10-2022-0175598

(51) Int. Cl.
*A61B 6/00* (2024.01)
*A61B 6/06* (2006.01)

(52) U.S. Cl.
CPC .............. *A61B 6/4405* (2013.01); *A61B 6/06* (2013.01)

(58) Field of Classification Search
CPC ... A61B 6/4405; A61B 6/4429; A61B 6/4447; A61B 6/06; A61B 6/08; G01N 2223/301;
(Continued)

(56) References Cited

U.S. PATENT DOCUMENTS

2006/0126792 A1   6/2006  Li
2017/0027532 A1*  2/2017  Joshi ...................... A61B 6/586

FOREIGN PATENT DOCUMENTS

KR   10-2017-0021723 A   2/2017
KR   10-2017-0062650 A   6/2017
KR     10-1812923 B1   12/2017

OTHER PUBLICATIONS

Korean Written Decision on Registration for KR 10-2022-0175598 dated May 8, 2023.
(Continued)

*Primary Examiner* — Don K Wong
(74) *Attorney, Agent, or Firm* — Sughrue Mion, PLLC

(57) ABSTRACT

Provided is a portable X-ray system is equipped with an X-ray tube mounted on one end portion of the photography stand with a structure extending to a predetermined height and changing a photographing direction and a photographing angle in a portable body moved by an operator to change an installation location, the portable X-ray system including a body mounted on one end portion of the photography stand and configured to change the photographing angle and form an exterior of the X-ray tube, a collimator mounted on one side surface of the body and configured to adjust an X-ray photographing area and an X-ray photographing direction, and a rotating connection part mounted between the body and the collimator and configured to couple the collimator to be rotated based on one side surface of the body and transmit power and an electrical signal transmitted from the body to the collimator.

4 Claims, 11 Drawing Sheets

(58) Field of Classification Search
CPC ....... G01N 2223/316; G01N 2223/308; G01N 2223/313; G01N 2223/314; G01N 2223/321
See application file for complete search history.

(56) References Cited

OTHER PUBLICATIONS

Korean Request for Submission of an Opinion for KR 10-2022-0175598 dated Mar. 2, 2023.

* cited by examiner

[Fig. 2]
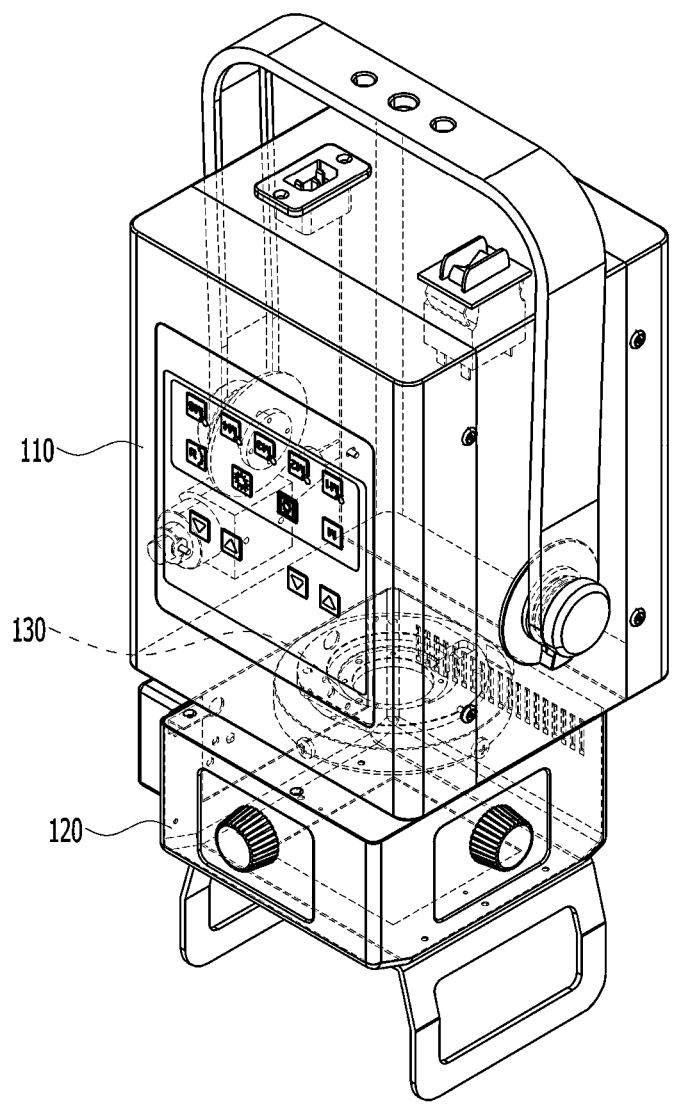

[Fig. 3]
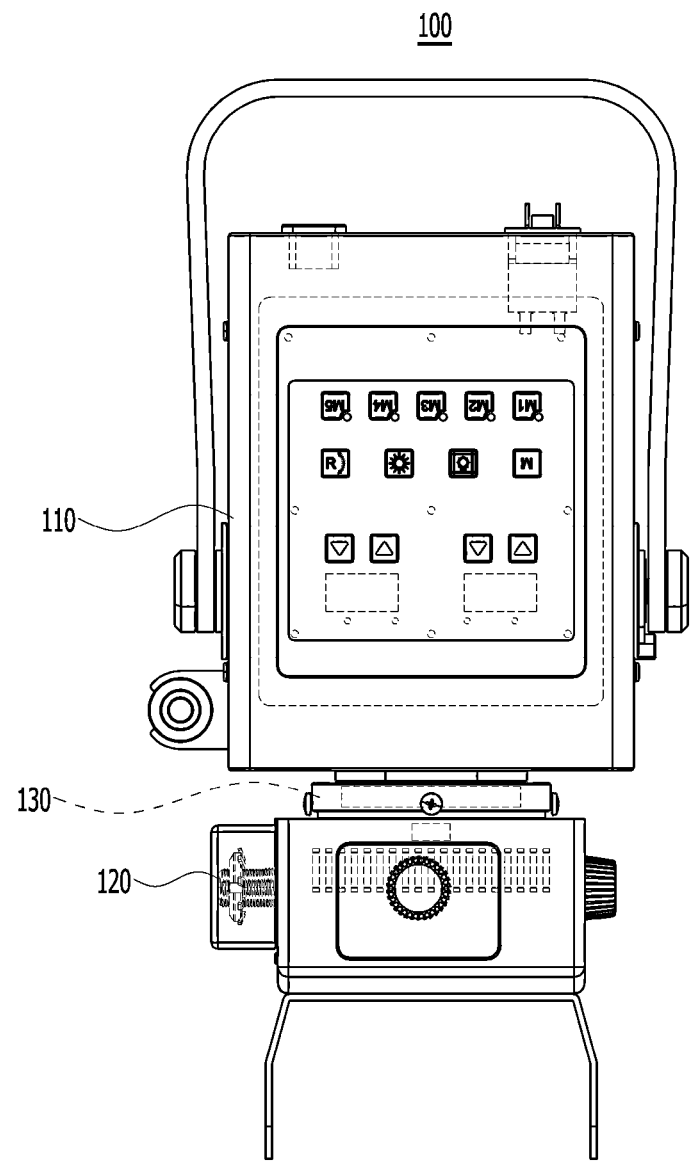

[Fig. 4]
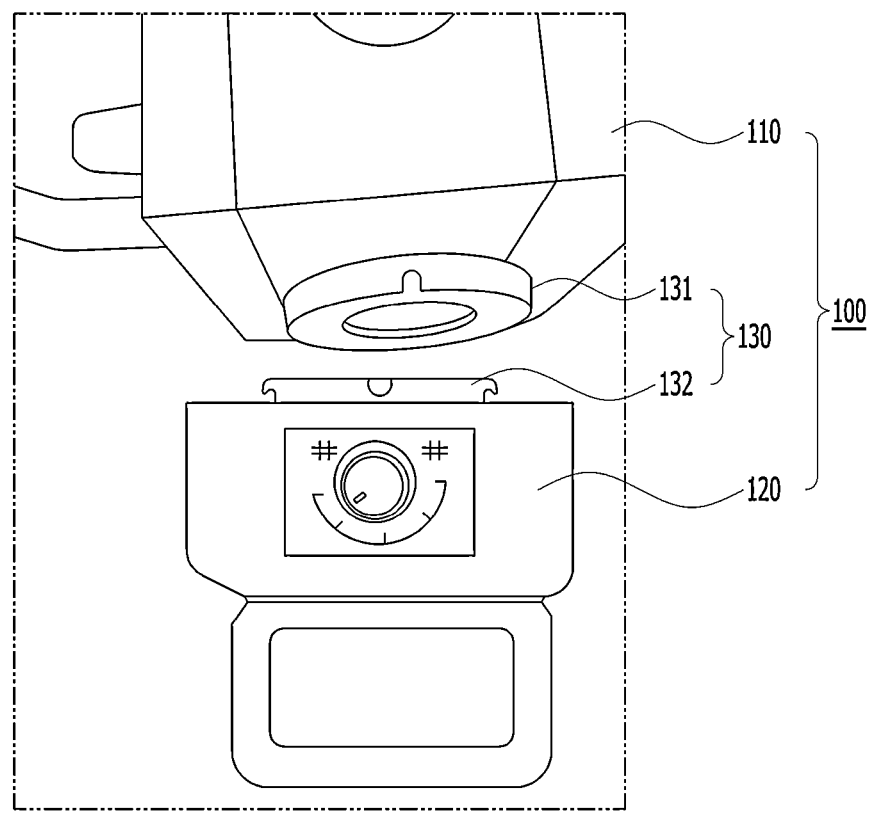

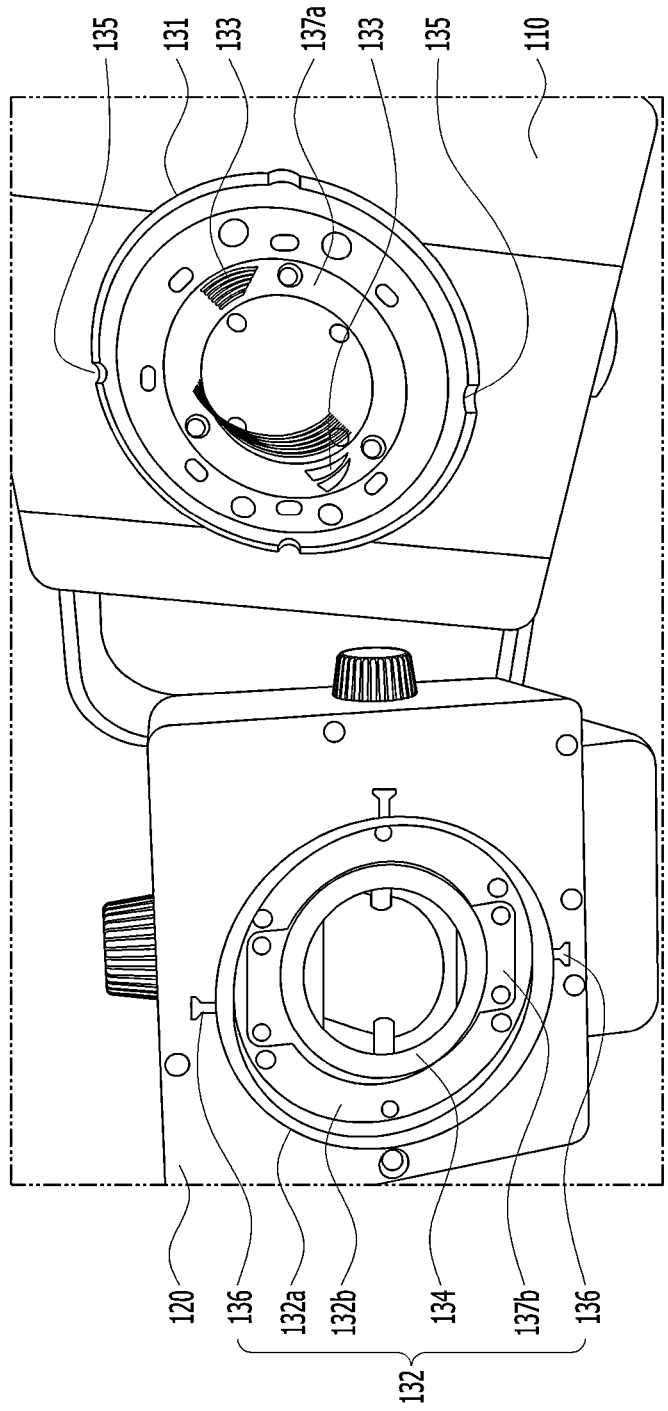
[Fig. 5]

[Fig. 6]
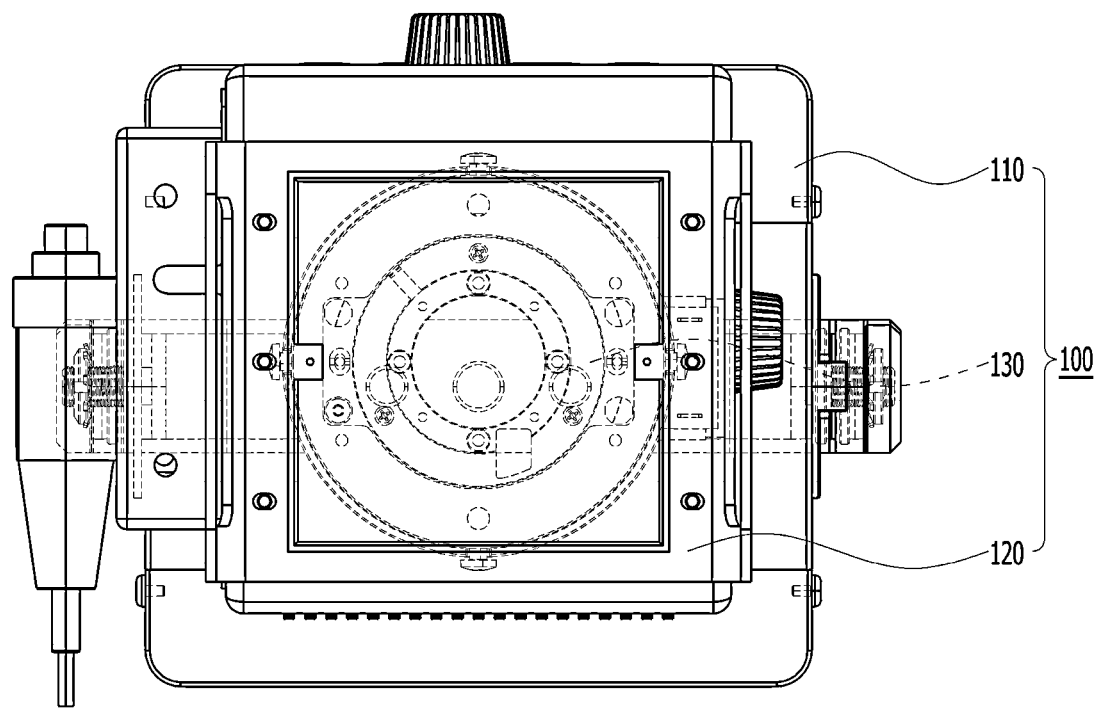

[Fig. 7]
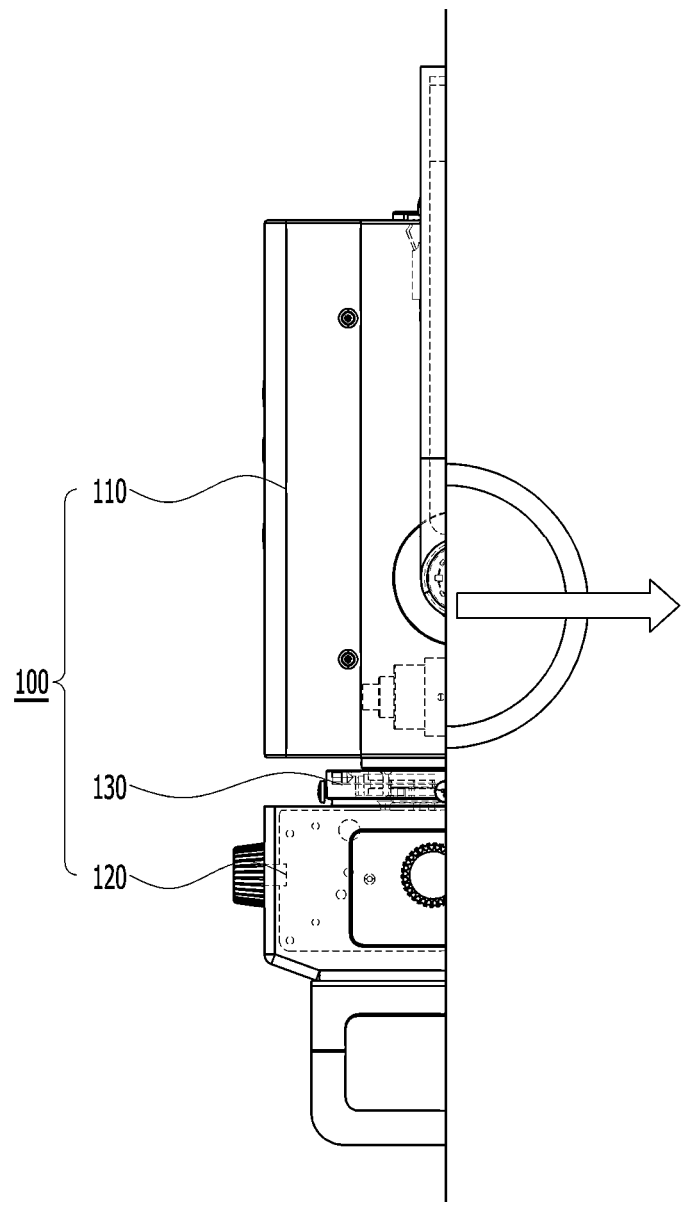

[Fig. 8]
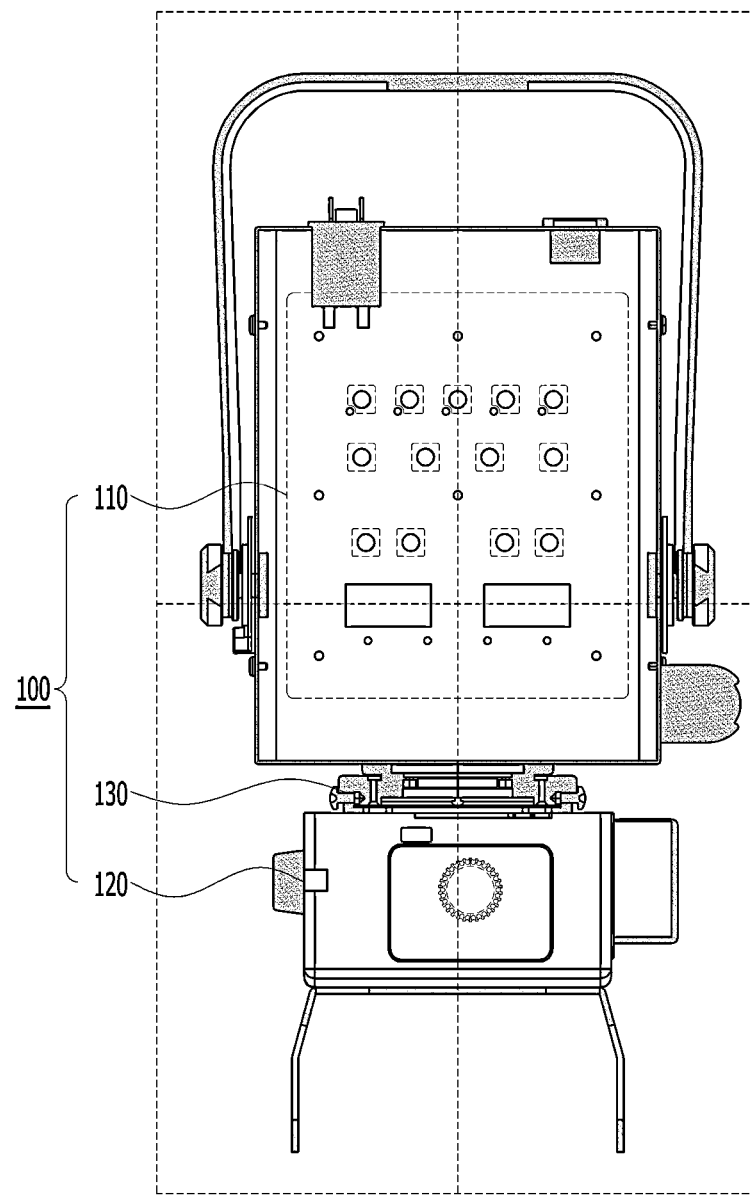

[Fig. 9]
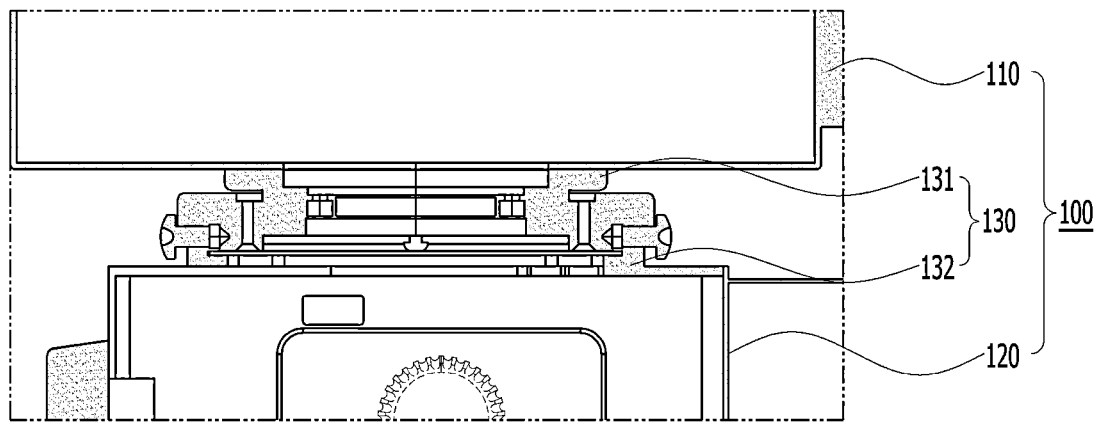

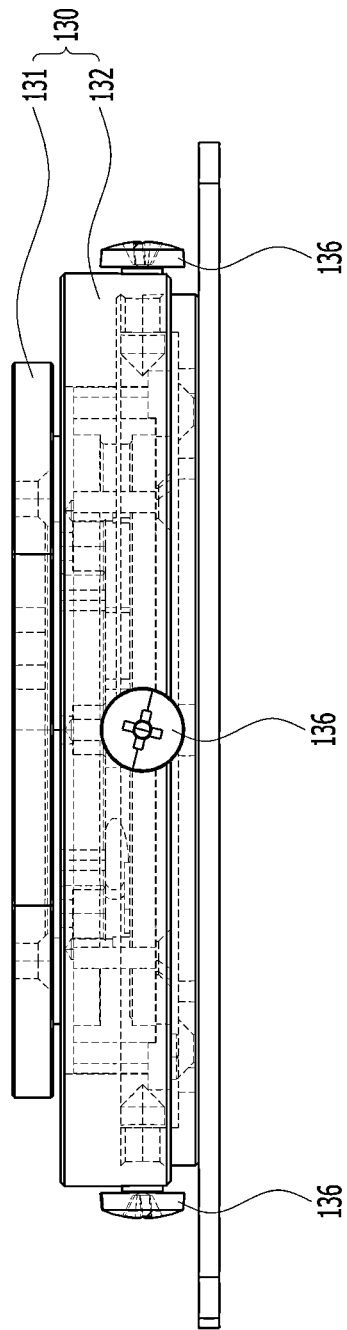
[Fig. 10]

[Fig. 11]
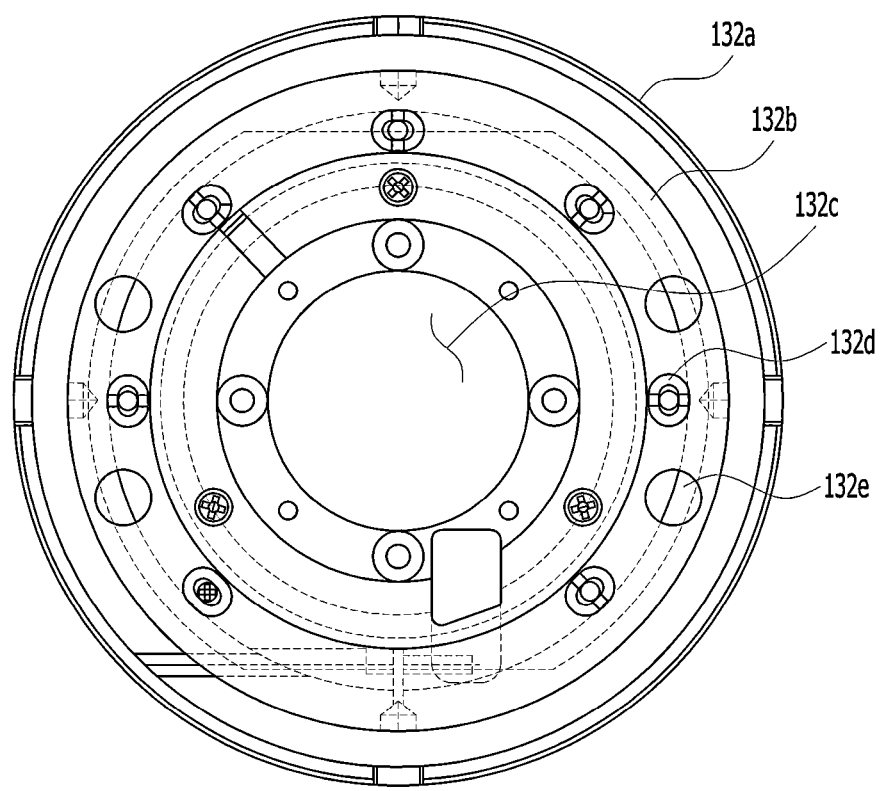

PORTABLE X-RAY SYSTEM WITH A CABLELESS COLLIMATOR CONNECTION STRUCTURE

CROSS REFERENCE TO RELATED APPLICATIONS

The present application is based on, and claims priority from the Korean Patent Application No. 10-2022-0175598, filed on Dec. 15, 2022, the entire contents of which are incorporated herein by reference.

STRUCTURE

Technical Field

The present invention relates to a portable X-ray system, and more particularly, to a portable X-ray system in which a rotation angle is unlimited because an electrical connection cable is omitted in a collimator connection structure.

BACKGROUND ART

Currently, when it is necessary to take X-rays directly in an emergency room or a clinic, a portable X-ray photography device is moved and used in the emergency room or clinic. The portable X-ray photography device includes a mobile body with wheels, and an X-ray tube articulately connected to the mobile body and equipped with an X-ray generator at an end of the X-ray tube, and the X-ray generator is freely movable by the X-ray tube with an intermediate section articulately connected to the mobile body.

A specific form and operation of the existing portable X-ray photography device 100 includes a structure shown in FIG. 1.

For most patients examined with the portable X-ray photographing device, a medical department requests X-ray photographing in a sitting position for various reasons, such as viewing air levels in the chest and abdomen or checking for fluid in the chest and pneumothorax. Therefore, in most cases, the examination is performed by raising the head of a bed to put the patient in a sitting posture, and thus a digital radiography (DR) image plate, which is an X-ray photographic original that should be positioned behind a patient's body, is obliquely disposed due to an inclination of a patient's bed to form an inclination angle.

However, in order to acquire an accurate X-ray image, an X-ray incidence angle of the X-ray generator at the end of the X-ray tube should be exactly perpendicular to the DR image plate, but as described above, when the DR image plate is obliquely disposed to form the inclination angle, it is very difficult to make the X-ray generator accurately perpendicular to the DR image plate even when the X-ray generator can be moved freely by the X-ray tube. Even when the DR image plate is parallel to a horizontal plane, an error in which the X-ray is not incident vertically on the DR image plate may occur when the X-ray generator is manipulated and disposed by hand.

In addition, as shown in FIG. 1, there is a limitation on a rotation angle of a collimator for adjusting an X-ray photographing direction due to externally exposed power and signal transmission/reception cables.

Therefore, there is a need for a technology capable of solving the above problems according to the related art.

RELATED ART DOCUMENT

Patent Document (Patent Document 1) Korean Registered Patent No. 10-1812923 (registered on Dec. 20, 2017)

DISCLOSURE

Technical Problem

The present invention is directed to providing a portable X-ray system in which an electrical connection cable may be omitted and a limitation on a rotation angle of a collimator may be removed in a collimator connection structure and which includes a configuration for maximizing operational efficiency.

Technical Solution

According to an aspect of the present invention, there is provided a portable X-ray system equipped with an X-ray tube mounted on one end portion of the photography stand with a structure extending to a predetermined height and changing a photographing direction and a photographing angle in a portable body moved by an operator to change an installation location, the portable X-ray system including a body mounted on one end portion of the photography stand and configured to change the photographing angle and form an exterior of the X-ray tube, a collimator mounted on one side surface of the body and configured to adjust an X-ray photographing area and an X-ray photographing direction, and a rotating connection part mounted between the body and the collimator and configured to couple the collimator to be rotated based on one side surface of the body and transmit power and an electrical signal transmitted from the body to the collimator.

The rotating connection part may include a first coupler which has a cylindrical structure formed to protrude from a center of one side surface of the body by a predetermined height and has a structure that rotates in place based on one side surface of the body and in which a plurality of fastening holes through which coupling fasteners are bolt-coupled are formed to be spaced at a predetermined angle along an outer circumferential surface of the first coupler; a second coupler with a ring structure which is formed to protrude from a center of one side surface of the collimator by a predetermined height and which is mounted in a form that surrounds an outer circumferential surface of the first coupler to be rotated together with the first coupler; a first connection terminal which is mounted at a center inside the first coupler and has a pogo pin structure protruding to a predetermined height and which is provided as a plurality of first connection terminals mounted to be spaced at different radii based on the center inside the first coupler and connected to a second connection terminal to transmit power and electrical signals to the collimator; a second connection terminal which is mounted at a center inside the second coupler and provided as a plurality of second connection terminals in a slip ring structure in which the plurality of second connection terminals are mounted to be spaced at different radii based on the center inside the second coupler and which accommodates the power and the electrical signals transmitted from the first connection terminals; and a coupling fastener which is provided as a plurality of coupling fasteners mounted to be spaced at a predetermined angle along an outer circumferential surface of the second coupler and has a structure bolt-coupled to the fastening hole of the first coupler to fasten the second coupler to the first coupler.

The rotating connection part may include a first substrate which is mounted at the center inside the first coupler, has a circular ring structure with a predetermined width, and has a printed circuit board structure with the first connection terminals mounted on an upper surface; and a second substrate which is mounted at the center inside the second coupler, has a circular ring structure with a predetermined width, and has a printed circuit board structure with the second connection terminals mounted on an upper surface.

The second coupler may include a fastening side wall forming portion with a planar ring structure protruding based on the center of one side surface of the collimator to form a side wall structure forming an internal space; a fastening side wall fixing portion which has a structure extending from an inner surface of the fastening side wall forming portion by a predetermined width in a central direction and is coupled to the collimator in surface contact with one side surface of the collimator to be fixed in a structure that is rotated by a predetermined angle based on a center of the second substrate; and an opening which is formed at a center of the fastening side wall fixing portion and has a structure communicating with a passing-through structure on one side surface of the collimator.

The second coupler may include a buffer fixing portion which is mounted on one side surface of the fastening side wall fixing portion and mounted on a fastening portion of the second substrate and has a structure with a predetermined amount of elastic restoring force to absorb an impact and a load applied from one side surface of the second substrate; and a spacing change portion mounted on one side surface of the fastening side wall fixing portion and configured to change a separation distance between the second substrate and the fastening side wall fixing portion.

Advantageous Effects

As described above, the portable X-ray system according to the present invention which includes a body of a specific structure, a collimator, and a rotating connection part, thereby including a configuration in which an electrical connection cable can be omitted from a connection structure of the collimator, thus removing a limitation on a rotation angle of the collimator, and maximizing operational efficiency, can be provided.

In addition, according to the portable X-ray system of the present invention, by providing the body of a specific structure, the collimator, and the rotating connection part, the portable X-ray system which easily adjusts an X-ray photographing area and an X-ray photographing direction without limitation on rotation of the collimator for adjusting the X-ray photographing direction, fundamentally prevents malfunctions due to damage to cables exposed to the outside, and maximizes the convenience of maintenance and management can be provided.

DESCRIPTION OF DRAWINGS

FIG. 2 is a perspective view illustrating a body, a collimator, and a rotating connection part of a portable X-ray system according to one embodiment of the present invention.

FIG. 3 is a front view illustrating the body, the collimator, and the rotating connection part of the portable X-ray system according to one embodiment of the present invention.

FIG. 4 is a photograph showing a state in which the body and the collimator of the portable X-ray system according to one embodiment of the present invention are separated.

FIG. 5 is a photograph showing the rotating connection part shown in FIG. 4.

FIG. 6 is a bottom view illustrating the body, the collimator, and the rotating connection part of the portable X-ray system according to one embodiment of the present invention.

FIG. 7 is a front view illustrating a state in which the centers of the body, the collimator, and the rotating connection part of the portable X-ray system according to one embodiment of the present invention are cut in a longitudinal direction.

FIG. 8 is a longitudinal cross-sectional view illustrating the portable X-ray system shown in FIG. 7.

FIG. 9 is a partially enlarged view illustrating the rotating connection part of FIG. 8.

FIG. 10 is a front view illustrating only the rotating connection part of the portable X-ray system according to one embodiment of the present invention.

FIG. 11 is a plan view illustrating a rotating connection part of a portable X-ray system according to another embodiment of the present invention.

MODES OF THE INVENTION

Figure 1:
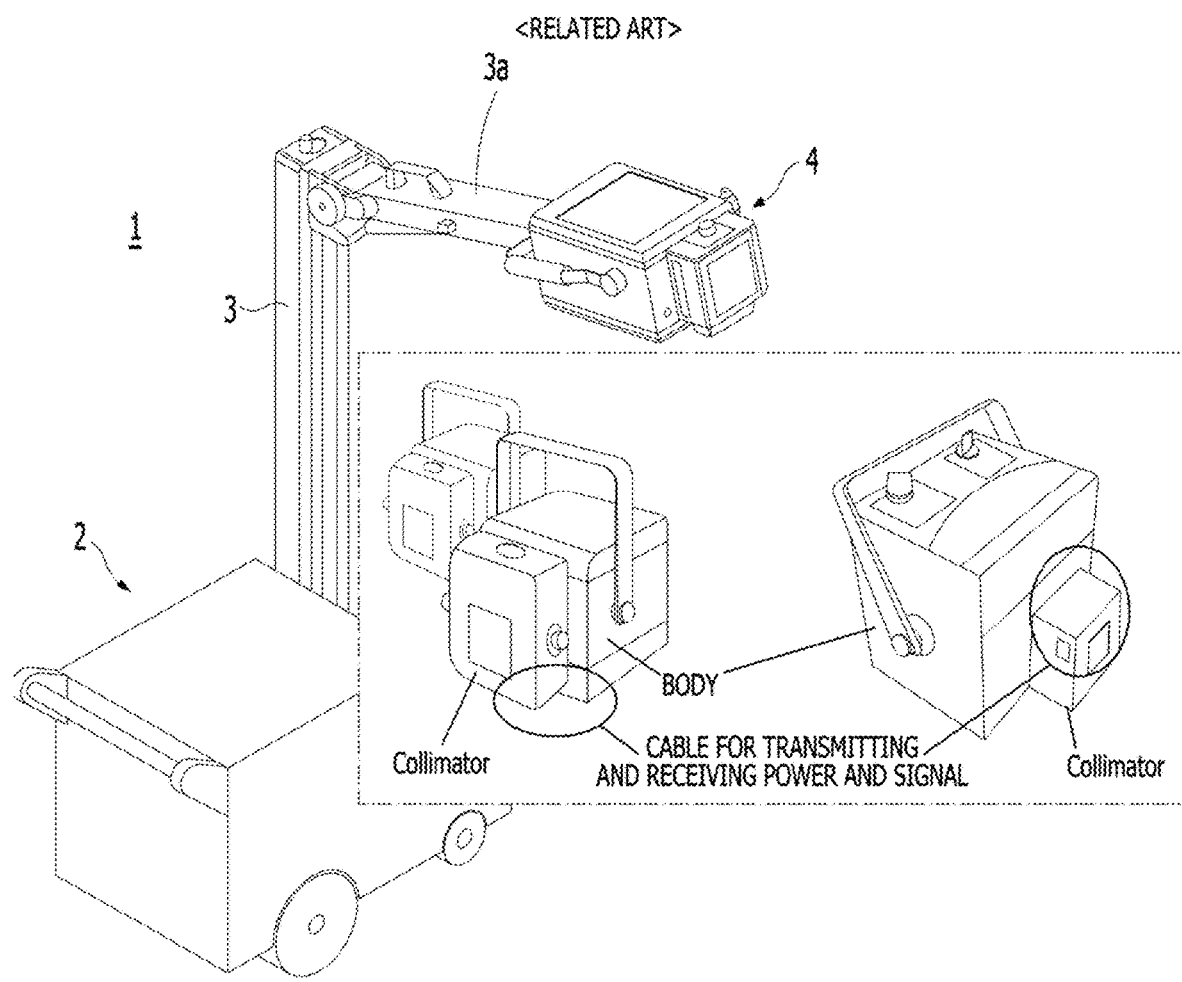
FIG. 1 shows a perspective view and a photograph illustrating a portable X-ray system according to the related art.

Hereinafter, exemplary embodiments of the present invention will be described in detail with reference to the accompanying drawings. Prior to description, the terms or words used in the present specification and the appended claims should not be construed as being limited to ordinary or dictionary meanings and should be construed with meanings and concepts consistent with the technical idea of the present invention.

Throughout the present specification, when a first member is referred to as being "on" a second member, this includes not only when the first member is in contact with the second member, but also when a third member is present between the first member and the second member. Throughout the present specification, when a part is referred to as "including" a component, this means that the part can include other elements, rather than excluding any other components unless specifically stated otherwise.

FIG. 2 is a perspective view illustrating a body, a collimator, and a rotating connection part of a portable X-ray system according to one embodiment of the present invention.

Referring to FIG. 2, a portable X-ray system 100 according to the present embodiment is a portable X-ray system in which an X-ray tube is mounted on one end portion of a photography stand with a movable body, which may be moved by the operator to change an installation site, and a structure extending to a predetermined height to change a photographing direction and a photographing angle. A portable X-ray system may be provided that includes a body 110 of a specific structure, a collimator 120, and a rotating connection part 130, thereby including a configuration in which an electrical connection cable can be omitted from a connection structure of the collimator 120, thus removing a limitation on a rotation angle of the collimator 120, and maximizing operational efficiency.

Hereinafter, each component constituting the portable X-ray system 100 according to the present embodiment will be described in detail with reference to the accompanying drawings.

FIG. 3 is a front view illustrating the body, the collimator, and the rotating connection part of the portable X-ray system according to one embodiment of the present invention, FIG. 4 is a photograph showing a state in which the body and the collimator of the portable X-ray system according to one embodiment of the present invention are separated, and FIG. 5 is a photograph showing the rotating connection part shown in FIG. 4.

FIG. 6 is a bottom view illustrating the body, the collimator, and the rotating connection part of the portable X-ray system according to one embodiment of the present invention, FIG. 7 is a front view illustrating a state in which the centers of the body, the collimator, and the rotating connection part of the portable X-ray system according to one embodiment of the present invention are cut in a longitudinal direction, FIG. 8 is a longitudinal cross-sectional view illustrating the portable X-ray system shown in FIG. 7, FIG. 9 is a partially enlarged view illustrating the rotating connection part of FIG. 8, and FIG. 10 is a front view illustrating only the rotating connection part of the portable X-ray system according to one embodiment of the present invention.

Referring to FIGS. 2 to 10, the body 110 of the portable X-ray system 100 according to the present embodiment is mounted on one end portion of a photography stand as a structure capable of changing a photographing angle and forms an exterior of an X-ray tube.

The collimator 120 of the portable X-ray system 100 according to the present embodiment is a component mounted on one side surface of the body 110 and has a structure for changing an X-ray photographing area and a photographing direction.

The rotating connection part 130 of the portable X-ray system 100 according to the present embodiment is a component mounted between the body 110 and the collimator 120 and has a structure coupling the collimator 120 to be rotated based on one side surface of the body 110 and transmitting power and an electrical signal from the body 110 to the collimator 120.

Specifically, as shown in FIGS. 4 and 5, the rotating connection part 130 may include a first coupler 131, a second coupler 132, a first connection terminal 133, a second connection terminal 134, and a coupling fastener 136, which each have a specific structure.

The first coupler 131 of the rotating connection part 130 is a cylindrical structure formed to protrude from the center of one side surface of the body 110 by a predetermined height and a structure capable of rotating in place based on one side surface of the body 110, in which a plurality of fastening holes 135 through which coupling fasteners 136 may be bolt-coupled are formed to be spaced at a certain angle along an outer circumferential surface of the first coupler 131. The second coupler 132 is a ring structure which is formed to protrude from the center of one side surface of the collimator 120 by a predetermined height and is mounted in a form that surrounds an outer circumferential surface of the first coupler 131 to be rotated together with the first coupler 131.

The first connection terminal 133 of the rotating connection part 130 is a component mounted at the center inside the first coupler 131 and has a pogo pin structure protruding to a predetermined height. The first connection terminal 133 may be provided as a plurality of first connection terminals 133 mounted to be spaced at different radii based on the center inside the first coupler 131 and connected to the second connection terminal 134 to transmit power and electrical signals to the collimator 120. The second connection terminal 134 is a component mounted at the center inside the second coupler 132. The second connection terminal 134 is provided as a plurality of second connection terminals 134 in a slip ring structure in which the plurality of second connection terminals 13 are mounted to be spaced at different radii based on the center inside the second coupler 132 and which accommodates the power and the electrical signals transmitted from the first connection terminals 133.

In addition, the coupling fastener 136 of the rotating connection part 130 is provided as a plurality of coupling fasteners 136 mounted to be spaced at a predetermined angle along the outer circumferential surface of the second coupler 132 and has a structure bolt-coupled to the fastening hole 135 of the first coupler 131 to fasten the second coupler 132 to the first coupler 131.

As shown in FIG. 5, the rotating connection part 130 may include a first substrate 137a and a second substrate 137b, which each have a specific structure.

Specifically, the first substrate 137a of the rotating connection part 130 is a component mounted at the center inside the first coupler 131, has a circular ring structure with a predetermined width, and has a printed circuit board structure with the first connection terminals 133 mounted on an upper surface. In addition, the second substrate 137b is a component mounted at the center inside the second coupler 132, has a circular ring structure with a predetermined width, and has a printed circuit board structure with the second connection terminals 134 mounted on an upper surface.

As shown in FIGS. 4 to 10, the second coupler 132 according to present embodiment may include a fastening side wall forming portion 132a, a fastening side wall fixing portion 132b, and an opening 132c, which each have a specific structure.

Specifically, the fastening side wall forming portion 132a of the second coupler 132 has a planar ring structure protruding based on the center of one side surface of the collimator 120 to form a side wall structure forming an internal space. The fastening side wall fixing portion 132b of the second coupler 132 has a structure extending from an inner surface of the fastening side wall forming portion 132a by a predetermined width in a central direction and is coupled to the collimator 120 in surface contact with one side surface of the collimator 120, and the fastening side wall fixing portion 132b is fixed in a structure that is rotated by a predetermined angle based on the center of the second substrate 137b. In addition, the opening 132c of the second coupler 132 is a component formed at the center of the fastening side wall fixing portion 132b and has a structure communicating with a passing-through structure on one side surface of the collimator 120.

FIG. 11 is a plan view illustrating a rotating connection part of a portable X-ray system according to another embodiment of the present invention.

Referring to FIG. 11 in comparison with FIG. 5, a second coupler 132 according to the present embodiment may include a buffer fixing portion 132d and a spacing change portion 132e, which each have a specific structure.

Specifically, the buffer fixing portion 132d of the second coupler 132 is a component mounted on one side surface of the fastening side wall fixing portion 132b and mounted on a fastening portion of the second substrate 137b and has a structure with a predetermined amount of elastic restoring force to absorb an impact and a load applied from one side surface of the second substrate 137b. In addition, the spacing change portion 132e of the second coupler 132 is a component mounted on one side surface of the fastening side wall fixing portion 132b and may change a separation distance between the second substrate 137b and the fastening side wall fixing portion 132b.

In this case, according to the present embodiment, a state in which a first connection terminal 133 and a second connection terminal 134 are electrically connected to each other may be kept in an optimal state.

Specifically, a position of the second substrate 137b on which the second connection terminal 134 is mounted may be adjusted to an optimal position using the spacing change portion 132e, and a pressing force or impact applied to the second connection terminal 134, which is pressed to be brought into contact by the first connection terminal 133, may be absorbed through the buffer fixing portion 132d. Consequently, with the above configuration, the state in which the first connection terminal 133 and the second connection terminal 134 are electrically connected to each other can be maintained in an optimal state, and furthermore, the portable X-ray system which maximizes convenience of maintenance and management and includes a configuration for maximizing operational efficiency can be provided.

As described above, the portable X-ray system which includes the body 110 of a specific structure, the collimator 120, and the rotating connection part 130, thereby including a configuration in which an electrical connection cable can be omitted from a connection structure of the collimator 120, thus removing a limitation on a rotation angle of the collimator 120, and maximizing operational efficiency, can be provided.

In addition, according to the portable X-ray system of the present invention, by providing the body 110 of a specific structure, the collimator 120, and the rotating connection part 130, the portable X-ray system which easily adjusts an X-ray photographing area and an X-ray photographing direction without limitation on rotation of the collimator 120 for adjusting the X-ray photographing direction, fundamentally prevents malfunctions due to damage to cables exposed to the outside, and maximizes the convenience of maintenance and management can be provided.

In the above detailed description of the present invention, only specific embodiments thereof are described. However, it should be understood that the present invention is not limited to the particular form described in the detailed description, but rather is understood to include all modifications, equivalents, and substitutes within the spirit and scope of the present invention as defined by the appended claims.

That is, the present invention is not limited to the specific embodiments and the descriptions, and various modifications can be made by those skilled in the art without departing from the gist of the present invention as claimed in the appended claims, and such modifications fall within the scope of protection of the present invention.

DESCRIPTION OF REFERENCE NUMERALS

100: Portable X-ray device
110: Body
120: Collimator
130: Rotating connection part
131: First coupler
132: Second coupler
132a: Fastening side wall forming portion
132b: Fastening side wall fixing portion
132c: Opening
132d: Buffer fixing portion
132e: Spacing change portion
133: First connection terminal
134: Second connection terminal
135: Fastening hole
136: Coupling fastener
137a: First substrate
137b: Second substrate

The invention claimed is:

1. A portable X-ray system equipped with an X-ray tube mounted on one end portion of a photography stand with a structure extending to a predetermined height and changing a photographing direction and a photographing angle in a portable body moved by an operator to change an installation location, the portable X-ray system comprising:
a body (110) mounted on one end portion of the photography stand and configured to change the photographing angle and form an exterior of the X-ray tube;
a collimator (120) mounted on one side surface of the body (110) and configured to adjust an X-ray photographing area and an X-ray photographing direction; and
a rotating connection part (130) mounted between the body (110) and the collimator (120) and configured to couple the collimator (120) to be rotated based on one side surface of the body (110) and transmit power and an electrical signal transmitted from the body (110) to the collimator (120),
wherein the rotating connection part (130) includes:
a first coupler (131) which has a cylindrical structure formed to protrude from a center of one side surface of the body (110) by a predetermined height and has a structure that rotates in place based on one side surface of the body (110) and in which a plurality of fastening holes (135) through which coupling fasteners (136) are bolt-coupled are formed to be spaced at a predetermined angle along an outer circumferential surface of the first coupler (131);
a second coupler (132) with a ring structure which is formed to protrude from a center of one side surface of the collimator (120) by a predetermined height and which is mounted in a form that surrounds an outer circumferential surface of the first coupler (131) to be rotated together with the first coupler (131);
a first connection terminal (133) which is mounted at a center inside the first coupler (131) and has a pogo pin structure protruding to a predetermined height and which is provided as a plurality of first connection terminals (133) mounted to be spaced at different radii based on the center inside the first coupler (131) and connected to a second connection terminal (134) to transmit power and electrical signals to the collimator (120);
a second connection terminal (134) which is mounted at a center inside the second coupler (132) and provided as a plurality of second connection terminals (134) in a slip ring structure in which the plurality of second connection terminals (134) are mounted to be spaced at different radii based on the center inside the second coupler (132) and which accommodates the power and the electrical signals transmitted from the first connection terminals (133); and
a coupling fastener (136) which is provided as a plurality of coupling fasteners (136) mounted to be spaced at a predetermined angle along an outer circumferential surface of the second coupler (132) and has a structure bolt-coupled to the fastening hole (135) of the first coupler (131) to fasten the second coupler (132) to the first coupler (131).

2. The portable X-ray system of claim 1, wherein the rotating connection part (130) includes:
  a first substrate 137a which is mounted at the center inside the first coupler (131), has a circular ring structure with a predetermined width, and has a printed circuit board structure with the first connection terminals (133) mounted on an upper surface; and
  a second substrate 137b which is mounted at the center inside the second coupler (132), has a circular ring structure with a predetermined width, and has a printed circuit board structure with the second connection terminals (134) mounted on an upper surface.

3. The portable X-ray system of claim 2, wherein the second coupler (132) includes:
  a fastening side wall forming portion (132a) with a planar ring structure protruding based on the center of one side surface of the collimator (120) to form a side wall structure forming an internal space;
  a fastening side wall fixing portion 132b which has a structure extending from an inner surface of the fastening side wall forming portion (132a) by a predetermined width in a central direction and is coupled to the collimator (120) in surface contact with one side surface of the collimator (120) to be fixed in a structure that is rotated by a predetermined angle based on a center of the second substrate (137b); and
  an opening (132c) which is formed at a center of the fastening side wall fixing portion (132b) and has a structure communicating with a passing-through structure on one side surface of the collimator (120).

4. The portable X-ray system of claim 3, wherein the second coupler (132) includes:
  a buffer fixing portion (132d) which is mounted on one side surface of the fastening side wall fixing portion (132b) and mounted on a fastening portion of the second substrate (137b) and has a structure with a predetermined amount of elastic restoring force to absorb an impact and a load applied from one side surface of the second substrate (137b); and
  a spacing change portion (132e) mounted on one side surface of the fastening side wall fixing portion (132b) and configured to change a separation distance between the second substrate (137b) and the fastening side wall fixing portion (132b).

* * * * *